US00PP13448P3

(12) United States Plant Patent
Cain

(10) Patent No.: US PP13,448 P3
(45) Date of Patent: Jan. 7, 2003

(54) GRAPEVINE CV. 'SUGRATWENTY'

(75) Inventor: David W. Cain, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 65 days.

(21) Appl. No.: 09/772,154

(22) Filed: Jan. 25, 2001

(65) Prior Publication Data

US 2002/0148018 P1 Oct. 10, 2002

(51) Int. Cl.[7] ..... A01H 5/00
(52) U.S. Cl. ..... Plt./205

(58) Field of Search ..... Plt./205

(56) References Cited

U.S. PATENT DOCUMENTS

PP5,056 P 5/1983 Olmo et al. ..... Plt./47

*Primary Examiner*—Bruce R. Campell
*Assistant Examiner*—Michelle Kizilkaya
(74) *Attorney, Agent, or Firm*—Knobbe, Martens, Olson & Bear

(57) ABSTRACT

A new and distinct grapevine variety characterized by extremely crisp, medium sized red seedless berries with an obovate shape. The variety is extremely productive when spur pruned, and produces very large, loose berry clusters.

1 Drawing Sheet

BACKGROUND AND SUMMARY OF THE INVENTION

This invention relates to the discovery and asexual propagation of a new variety of grapevine, *Vitis vinifera* cv. 'Sugratwenty'. The new variety was first hybridized by David W. Cain in Wasco, Kern County, Calif., the variety being originated by controlled hybridization. The new variety is characterized by producing red, obovate, extremely crisp, medium sized seedless berries which increase in size in response to exogenously applied gibberellic acid. The new variety produces very large, naturally loose clusters and is extremely productive when spur pruned.

The seed parent is the 'Christmas Rose' (U.S. Plant Pat. No. 5,056) variety. The pollen parent is the 'U.S. Department of Agriculture selection B31-164' variety. The parent varieties were first crossed in May, 1989, with the date of first flowering being May, 1991. The new 'Sugratwenty' variety was first asexually propagated by David W. Cain near Wasco, Kern County, Calif., in December, 1991 by using cuttings.

The new grapevine variety cv. 'Sugratwenty' resembles its seed parent the 'Christmas Rose' in outward appearance. It differs from the 'Christmas Rose' variety by possessing vestigial seed traces rather than fully developed, hard seeds. It also differs from its seed parent the 'Christmas Rose' by having smaller berries which color with more difficulty. The new variety 'Sugratwenty' differs from its pollen parent, the unnamed, nonpatented 'B31-164' by having smaller, less-lignified seed remnants and obovate rather than round berries which ripen later.

'Sugratwenty' is distinguished from other commonly grown red seedless grapes such as the 'Crimson' (nonpatented) variety and the 'Ruby Seedless' (nonpatented) variety. The new variety 'Sugratwenty' most nearly resembles the 'Crimson' variety, but differs from 'Crimson' by possessing a more fruitful but less vigorous vine. The berries of 'Sugratwenty' are more broadly obovate than the narrow, elongated, cylindrical berries of 'Crimson'. Additionally, 'Sugratwenty' produces clusters that are larger and looser than in the 'Crimson' variety.

The new variety 'Sugratwenty' differs from the 'Ruby Seedless' variety by producing larger, firmer berries. It also is distinguished from the 'Ruby Seedless' variety in that the berries attain a much brighter, less blackish-red coloration but are more difficult to color than the berries of the 'Ruby Seedless' variety.

The new 'Sugratwenty' variety has been shown to maintain its distinguishing characteristics through successive propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
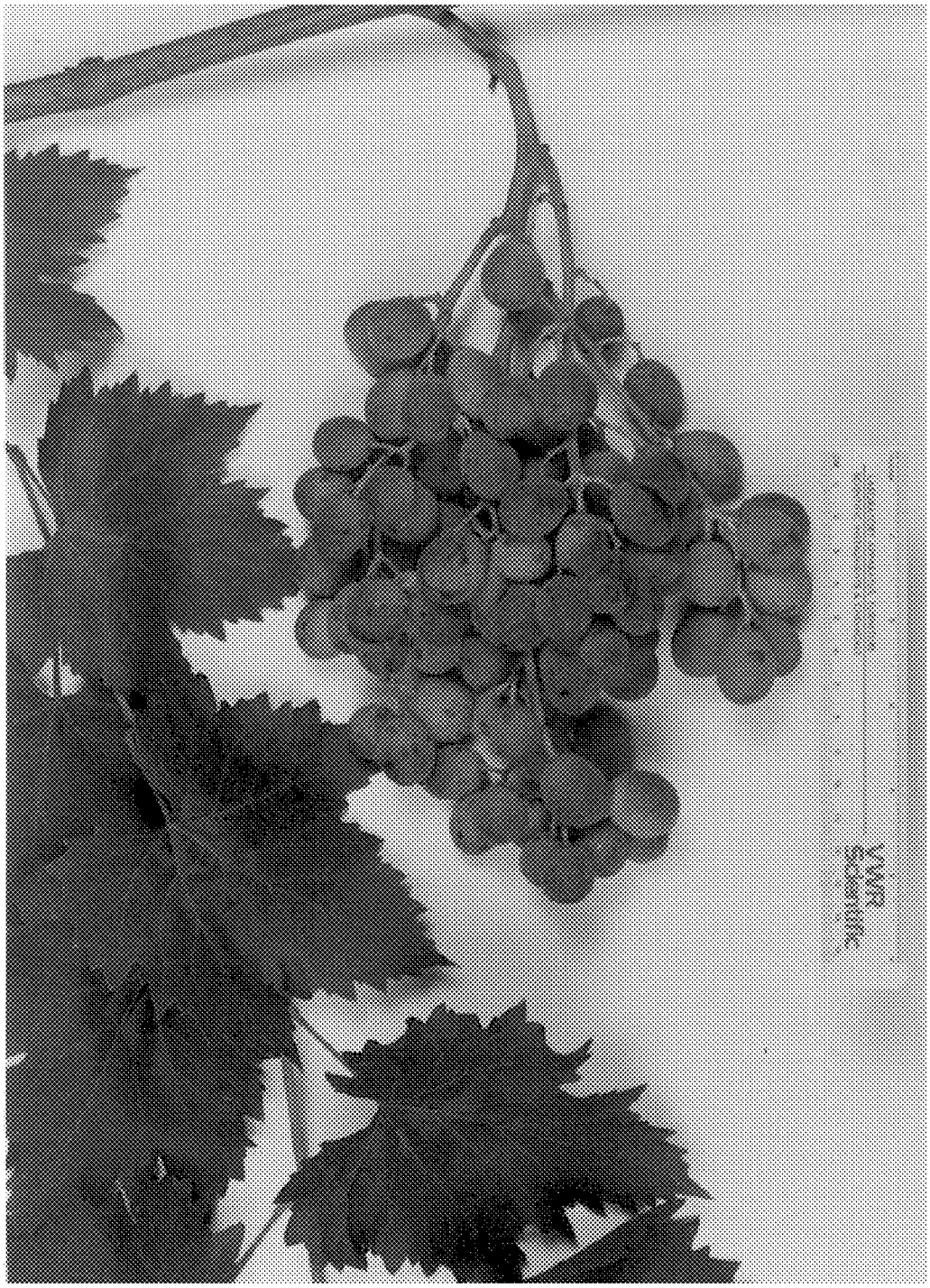

Throughout this specification, color names beginning with a small letter signify that the name of that color, as used in common speech, is aptly descriptive. Color names beginning with a captial letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwenty' plants grown in the vicinity of Wasco, Kern County, Calif., during 1999–2000, and is believed to apply to plants of the variety grown under similar conditions of soil and climate elsewhere.

VINE

General:
*Size.*—Medium-small.
*Vigor.*—Medium.
*Density of foliage.*—Medium-open.
*Productivity.*—Very productive.
*Root stock.*—Own root.

Trunk:
*Shape.*—Medium.
*Straps.*—Short, split.
*Surface texture.*—Shaggy.
*Inner bark color.*—About 176C.

SHOOTS

Young shoot:
*Form of tip.*—Half-open.
*Distribution of anthocyanin coloration of tip.*—Piping (striped).
*Intensity of anthocyanin coloration of tip.*—Weak.
*Density of prostrate hairs on tip.*—Very sparse.
*Density of erect hairs on tip.*—Absent.

Flowering shoot:
*Vigor during flowering.*—Weak to medium.
*Attitude during flowering on shoots which are not tied.*—Semi-erect.
*Color of dorsal side of internodes.*—Green with red stripes; about 183A.
*Color of ventral side of internodes.*—About green 144A.
*Color of dorsal side of nodes.*—Green with red stripes; about 183A.
*Color of ventral side of nodes.*—About green 144A.
*Density of erect hairs on nodes.*—None.
*Erect hairs on internode.*—Absent.
*Density of prostrate hairs on nodes.*—None.
*Density of prostrate hairs on internodes.*—Absent.
*Anthocyanin coloration of buds.*—Absent or very weak.

Tendrils:
*Distribution on the shoot at full flowering.*—Discontinuous.
*Thickness.*—Thin.
*Color.*—About 145A.
*Form.*—Mostly bifurcated — occasionally trifurcated.
*Number of consecutive tendrils.*—Up to two.
*Length of tendril.*—Medium, about 23.0 cm.

LEAVES

Young leaves:
*Color of upper surface of first 4 distal unfolded leaves.*—About reddish 182B.
*Average intensity of anthocyanin coloration of six distal leaves prior to flowering.*—weak.
*Density of prostrate hairs between veins at lower surface of 4th distal unfolded leaf.*—Absent.
*Density of erect hairs between veins at lower surface of 4th distal unfolded leaf.*—Absent.
*Density of prostrate hairs on veins at lower surface of 4th distal unfolded leaf.*—Absent — very sparse.
*Density of erect hairs on veins at lower surface of 4th distal unfolded leaf.*—Absent.

Mature leaves:
*Average length.*—About 15.6 cm.
*Average width.*—About 18.3 cm.
*Size of blade.*—Medium.
*Shape of blade.*—Pentagonal.
*Number of lobes.*—3.
*Anthocyanin coloration of main veins on the upper side of the blade.*—Absent.
*Mature leaf profile.*—Flat.
*Blistering surface of blade upper surface.*—Absent.
*Leaf blade tip.*—In the plane of the leaf.
*Undulation of margin.*—Pronounced.
*Apex.*—Cuspidate.
*Thickness.*—Medium.
*Undulation of blade between main and lateral veins.*—Absent.
*Shape of teeth.*—Both sides straight.
*Length of teeth.*—Medium. No data available.
*General shape of petiole sinus.*—Open.
*Tooth at petiole sinus.*—Present.
*Petiole sinus limited by veins.*—Absent.
*Shape of upper lateral sinus.*—Open.
*Depth of upper lateral sinus.*—Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—None.
*Density of erect hairs on main veins on lower surface of blade.*—None or very sparse.
*Density of prostrate hairs on main veins on upper surface of blade.*—Absent.
*Autumn coloration of leaves.*—About yellow 11B (changes very late, frost usually kills leaves before color change occurs).

Upper surface:
*Color.*—About 147A.
*Surface texture.*—Smooth.
*Surface appearance.*—Dull.
*Goffering of blade.*—Absent.

Lower surface:
*Color.*—About 147B.
*Anthocyanin coloration of main veins on lower leaf surface.*—Weak.
*Glossiness.*—Weak.
*Pubescence.*—Absent.
*Surface texture.*—Smooth.
*Surface appearance.*—Semi-glossy.

Petiole:
*Length of petiole.*—About 14.4 cm.
*Length of petiole compared to middle vein.*—Slightly shorter.
*Density of prostrate hairs on petiole.*—None.
*Density of erect hairs on petiole.*—None.
*Shape of base of petiole sinus.*—U-shaped.

Woody shoot:
*Shape.*—Medium.
*Internode length.*—Medium, about 117.8 mm.
*Width at node.*—About 18.0 mm.
*Cross section.*—Circular.
*Surface.*—Smooth.
*Main color.*—Yellowish brown, about 165D Greyed-Orange group.
*Lenticels.*—Absent.
*Density of erect hairs on nodes.*—None.
*Density of erect hairs on internodes.*—None.
*Growth of axillary shoots.*—Weak, about 159.8 cm.

Buds:
*Shape.*—Pointed.
*Size.*—Small; 6.6 mm length by 4.0 mm width.
*Position.*—45° angle.

*Cane bud fruitfulness.*—Basal most fruitful.
*Time of bud burst.*—Medium.

FLOWERS

General:
*Flower sex.*—Hermaphrodite.
*Length of first inflorescence.*—Very long; about 30.9 cm.
*Position of first flowering node.*—$4^{th}$.
*Number of infloresences per shoot.*—2.
*Date of full bloom.*—May 3, 2000.
*Time of bloom.*—Late, as compared with similar varieties in the growing area of Wasco, Kern County, Calif..
*Size* (*diameter of fully open flower*).—Large.

FRUIT

General:
*Ripening period.*—Late, about 30 days after 'Thompson Seedless' variety.
*Use.*—Fresh market.
*Keeping quality.*—Good.
*Resistance.*—Insects: medium (typical of *Vitis vinifera*). Diseases: medium (typical of *Vitis vinifera*).
*Shipping quality.*—Good.
*Date of first harvest.*—Sep. 1, 2000.
*Solids-sugar.*—High (~21%).
*Refractometer test.*—23.3° brix.
*Acid.*—Low, about 45 g/L tartaric acid.
*Juice pH.*—About 4.12 (on Oct. 13, 2000).

Cluster:
*Bunch size* (*peduncle excluded*).—Very large.
*Bunch length* (*peduncle excluded*).—Very long, about 31.9 cm by 14.9 cm.
*Bunch width.*—About 14.9 cm.
*Bunch weight.*—High, averaging about 728 g.
*Bunch density.*—Very loose.
*Number of berries.*—About 209.
*Form.*—Cylindrical.

Peduncle:
*Length of peduncle.*—Very long, about 5.81 cm.
*Lignification of peduncle.*—Medium.
*Color.*—About 145A.

Berry:
*Size.*—Medium.
*Uniformity of size.*—Uniform.
*Berry weight.*—Medium, about 3.56 g.
*Shape.*—Obovate.
*Presence of seeds.*—Rudimentary, about 1.33 mg/seed.
*Cross section.*—Circular.
*Dimensions.*—Longitudinal axis 20.7 mm, horizontal axis 17.6 mm.
*Skin color* (*without bloom*).—About red-grey 187B.
*Coloration of flesh.*—None.
*Juiciness of flesh.*—Very slightly juicy.
*Berry firmness.*—Firm.
*Particular flavor.*—None.
*Bloom* (*cuticular wax*).—Medium to strong.
*Pedicel length.*—Long, about 6.82 mm.
*Berry separation from pedicel.*—Medium.
*Visibility of hilum.*—Slightly clear.

Skin:
*Thickness.*—Thin.
*Texture.*—Tender.
*Reticulation.*—Absent.
*Roughness.*—Absent.
*Tenacity.*—Tenacious to flesh.
*Tendency to crack.*—None.

What is claimed is:

1. A new and distinct variety of grapevine cv. 'Sugratwenty' as herein illustrated and described.

* * * * *